United States Patent
Whisler et al.

(10) Patent No.: US 11,602,589 B2
(45) Date of Patent: Mar. 14, 2023

(54) PERISTALTIC PUMPS WITH SELECTIVE ACTIVATION OF MULTIPLE FLUID LINES AND FLUID MANAGEMENT SYSTEMS INCLUDING THE SAME

(71) Applicant: COVIDIEN LP, Mansfield, MA (US)

(72) Inventors: Jordan A. Whisler, Brookline, MA (US); Roman J. Jedras, Woburn, MA (US)

(73) Assignee: COVIDIEN LP, Mansfield, MA (US)

( * ) Notice: Subject to any disclaimer, the term of this patent is extended or adjusted under 35 U.S.C. 154(b) by 853 days.

(21) Appl. No.: 16/418,739

(22) Filed: May 21, 2019

(65) Prior Publication Data
US 2020/0368406 A1 Nov. 26, 2020

(51) Int. Cl.
| | | |
|---|---|---|
| *A61M 3/02* | (2006.01) | |
| *A61M 1/00* | (2006.01) | |
| *A61B 18/00* | (2006.01) | |
| *A61B 17/42* | (2006.01) | |

(52) U.S. Cl.
CPC ............ *A61M 3/0208* (2014.02); *A61M 1/77* (2021.05); *A61M 1/80* (2021.05); *A61M 3/0229* (2013.01); *A61M 3/0258* (2013.01); *A61B 17/42* (2013.01); *A61B 2018/00559* (2013.01); *A61B 2217/007* (2013.01); *A61M 2205/3337* (2013.01)

(58) Field of Classification Search
CPC ...... F04B 43/12; F04B 43/1292; F04B 49/00; A61M 39/10
See application file for complete search history.

(56) References Cited

U.S. PATENT DOCUMENTS

| | | | | |
|---|---|---|---|---|
| 3,951,570 A | * | 4/1976 | De Biaggi | F04B 9/02 417/319 |
| 4,365,943 A | * | 12/1982 | Durrum | F04B 43/086 417/429 |
| 4,441,867 A | * | 4/1984 | Berelson | F04B 43/1292 417/475 |
| 4,871,262 A | * | 10/1989 | Krauss | G05D 11/133 366/160.3 |
| 5,738,644 A | * | 4/1998 | Holmes | A61M 1/3624 604/4.01 |
| 5,799,832 A | * | 9/1998 | Mayo | A23G 9/281 222/135 |
| 6,376,113 B1 | * | 4/2002 | Edlund | H01M 8/04022 429/410 |
| 7,300,264 B2 | * | 11/2007 | Souza | B41J 2/17596 417/477.11 |
| 8,277,196 B2 | * | 10/2012 | Lewis | F04B 43/1276 417/1 |

(Continued)

*Primary Examiner* — Scott J Medway
(74) *Attorney, Agent, or Firm* — Carter DeLuca & Farrell LLP (57) ABSTRACT

A peristaltic pump includes a first motor shaft, a second motor shaft, a first pump head, a second pump head, and a motor. The first pump head is operably coupled to the first motor shaft such that the first pump head is rotated in response to rotation of the first motor shaft. The second pump head is operably coupled to the second motor shaft such that the second pump head is rotated in response to rotation of the second motor shaft. The motor is configured to rotate the first and second motor shafts. The pump head has a first mode in which the first pump head is rotated and the second pump head is idle and a second mode in which the first pump head is idle and the second pump head is rotated.

9 Claims, 6 Drawing Sheets

(56) References Cited

U.S. PATENT DOCUMENTS

| | | |
|---|---|---|
| 8,591,464 B2 | 11/2013 | Kumar et al. |
| 9,084,847 B2 | 7/2015 | Klein et al. |
| 9,504,784 B2 * | 11/2016 | Ozturk ................ F04B 43/1253 |
| 9,518,576 B1 * | 12/2016 | Wiederin ........... A61M 5/14232 |
| 10,537,671 B2 * | 1/2020 | Wilt ........................ F04B 49/06 |
| 2002/0150476 A1 * | 10/2002 | Lucke .................... A61M 1/00 417/2 |
| 2003/0039728 A1 * | 2/2003 | Herrick ................ B67D 1/0857 426/249 |
| 2007/0068969 A1 * | 3/2007 | Orzech ................. F04B 43/082 222/214 |
| 2007/0148022 A1 * | 6/2007 | Cheng ................ F04B 43/1253 417/477.1 |
| 2007/0161970 A1 * | 7/2007 | Spohn ............... A61M 5/14546 604/533 |
| 2007/0206070 A1 * | 9/2007 | Morgan ............... B41J 2/17509 347/85 |
| 2009/0035165 A1 * | 2/2009 | Chang ................ F04B 43/1292 417/477.2 |
| 2009/0047185 A1 * | 2/2009 | Fennimore .............. C01B 3/065 422/129 |
| 2010/0116375 A1 * | 5/2010 | Eginton .................. F04B 23/10 141/9 |
| 2011/0238018 A1 * | 9/2011 | McKenzie-Butler ........................ A61M 5/1414 604/257 |
| 2012/0104045 A1 * | 5/2012 | Chang ...................... A61J 1/20 222/145.5 |
| 2015/0104329 A1 * | 4/2015 | Chin .................... F04B 49/007 417/53 |
| 2015/0297830 A1 * | 10/2015 | Okiyama ............... A61M 39/28 604/250 |
| 2016/0067144 A1 * | 3/2016 | Chang .................. A61M 39/10 604/92 |
| 2017/0055810 A1 | 3/2017 | Germain et al. |
| 2017/0210064 A1 | 7/2017 | Aw et al. |

* cited by examiner

PERISTALTIC PUMPS WITH SELECTIVE ACTIVATION OF MULTIPLE FLUID LINES AND FLUID MANAGEMENT SYSTEMS INCLUDING THE SAME

BACKGROUND

1. Technical Field

The present disclosure relates to peristaltic pumps, fluid management systems, and methods for controlling the same and, more specifically, peristaltic pumps with selective activation of multiple fluid lines and fluid management systems for maintaining a desired pressure within a body cavity.

2. Discussion of Related Art

During endoscopic, hysteroscopic, and laparoscopic procedures, a body cavity is distended to improve visualization and access to areas within the body cavity. A pump is used to provide fluid into the body cavity to distend the body cavity. In addition, an outflow line by be used to allow fluid to flow from the body cavity to prevent the body cavity from being overly distended.

For example, when using a hysteroscopic approach, the uterine cavity is distended to assist in viewing uterine walls. A fluid management system is used to distend the uterus to provide a working space by expanding or distending the uterine cavity with one or more fluids. A fluid management system may include a single inflow line driven by a pump, e.g., a peristaltic pump, and two outflow lines. The outflow lines are used to maintain a desired pressure within the uterus by allowing excess fluid to flow from within the uterus. One of the outflow lines is drawn by atmospheric pressure and the other is drawn by a vacuum pump.

There is a continuing need for improved systems and methods for maintaining a desired pressure within a body cavity during endoscopic, hysteroscopic, and laparoscopic procedures.

SUMMARY

In an aspect of the present disclosure, a peristaltic pump includes a first motor shaft, a second motor shaft, a first pump head, a second pump head, and a motor. The first pump head is operably coupled to the first motor shaft such that the first pump head is rotated in response to rotation of the first motor shaft. The second pump head is operably coupled to the second motor shaft such that the second pump head is rotated in response to rotation of the second motor shat. The motor is configured to rotate the first and second motor shafts. The pump head has first mode in which the first pump head is rotated and the second pump head is idle and a second mode in which the first pump head is idle and the second pump head is rotated.

In aspects, the first motor shaft is a first portion of a common motor shaft and the second motor shaft is a second portion of the common motor shaft. The first pump head may be on a first side of the motor and the second pump head is on a second opposite side of the motor.

In some aspect, the pump includes a first clutch having a motor side operably coupled to the first motor shaft and a drive side operably coupled to the first pump head. The first clutch may have an engaged configuration in which the first pump head rotates in response to rotation of which the first drive shaft and a disengaged configuration in which the first pump head is decoupled from rotation of the first drive shaft. The first clutch may be in the disengaged configuration when the motor is in the second mode.

In certain aspects, the pump includes a second clutch having a motor side operably coupled to the second motor shaft and a drive side operably coupled to the second pump head. The second clutch having an engaged configuration in which the second pump head rotates in response to rotation of the second drive shaft and a disengaged configuration in which the second pump head is decoupled from rotation of the second drive shaft. The pump may include a gear box that is coupled tot the first motor shaft and the drive side of the first clutch. The gear box may apply a gear ratio to rotation of the first motor shaft such that rotation of the drive side of the first clutch is different than rotation of the first motor shaft.

In particular aspects, the motor has a third mode in which the first pump head and the second pump head are rotated. In the third mode the first pump head may rotate at a different speed than the second pump head. The first pump head may have a first diameter and the second pump head may have a second diameter different from the first diameter. The first and second pump head may each be configured to compress an outer wall of a tube passed through the respective pump head such that a fluid within the tube is advanced through the tube as the respective pump head is rotated.

In another aspect of the present disclosure, a fluid management system include an inflow pump, an inflow path, a first outflow path, a second outflow path, a first pump head, and a second pump head. The first inflow path is in fluid communication with the inflow pump and is configured to deliver a fluid from the inflow pump into a body cavity. The first outflow path is configured to be in selective fluid communication with the body cavity. The second outflow path is configured to be in selective fluid communication with the body cavity. The first pump head is configured to pump fluid through the first outflow path and the second pump head is configured to pump fluid through the second outflow path. The first and second pump heads are selectively rotatable to maintain a desired pressure within the body cavity.

In aspects, the fluid management system includes an outflow pump including a first motor shaft, a second motor shaft, and a motor. The first motor shaft is operably coupled to the first pump head such that the first pump head is rotated in response to rotation of the first motor shaft. The second motor shaft is operably coupled to the second pump head such that the second pump head is rotated in response to rotation of the second motor shaft. The motor is configured to rotate the first and second motor shafts. The pump has a first mode in which the first pump head is rotated and the second pump head is idle and a second mode in which the first pump head is idle and the second pump head is rotated. The fluid management system may include a controller in communication with the outflow pump that is configured to control the mode of the motor. The fluid management system may include a primary outflow path that is configured to be in directly fluid communication with the body cavity and each of the first and second outflow paths to fluidly connect the first and second outflow paths with the body cavity. The fluid management system may include a first clutch in mechanical communication with the motor and the first pump head, wherein when the first clutch is engaged the first pump head is rotated, and when the first clutch is disengaged, the first pump head is idle. The fluid management system may include a second clutch in mechanical communication with the motor and the second pump head, wherein when the second clutch is engaged the second pump head is rotated, and when the second clutch is disengaged, the second pump head is idle.

In another aspect of the present disclosure, a method of controlling a fluid management system with a controller of the fluid management system includes selecting a first outflow path associated with a first pump head of an outflow path, activating the outflow pump tor rotate the first pump head, and switching from the first outflow path to a second outflow path different from the first outflow path and activating the outflow pump to rotate a second pump head associated with the second outflow path.

In aspects, activating the outflow pump to rotate the first pump head includes disengaging a first clutch associated with the first pump head and activating the outflow pump to rotate the second pump head includes disengaging a second clutch associated with the second pump head and engaging the first clutch associated with the first pump head. Selecting the first outflow path may include operating a switch to open the first outflow path and close the second outflow path.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closer to the clinician and the term "distal" refers to the portion of the device or component thereof that is farther from the clinician.

Figure 1:
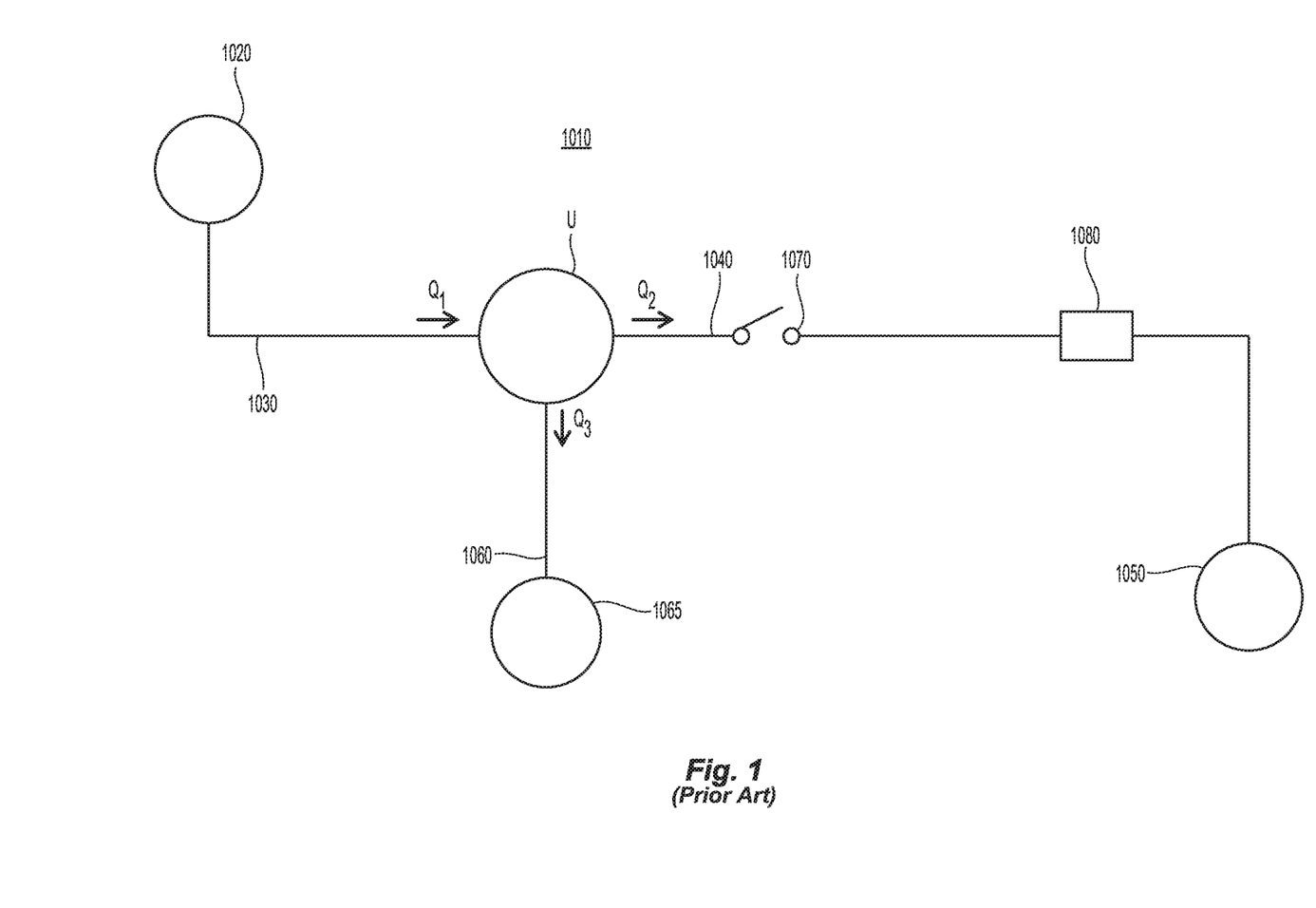
FIG. 1 is a schematic of a prior art fluid management system for managing intrauterine pressure within a uterus.

Referring now to FIG. 1, a schematic of a prior art fluid management system 1010 that is configured to distend a uterus U and maintain a desired pressure within the uterus U of a patient is provided. The fluid management system 1010 includes an inflow pump 1020, an inflow path 1030, a first outflow path 1040, a second outflow path 1060, and an outflow or vacuum pump 1050. The inflow pump 1020 is configured to provide a constant flow of fluid $Q_1$ into the uterus U through the inflow path 1030 to distend the uterus U. The first outflow path 1040 is fluidly coupled to the outflow pump 1050 which is configured to provide a vacuum such that an outflow of fluid $Q_2$ flows from the uterus U. The first outflow path 1040 may include a switch 1070 in the form of a shutoff, a valve, or another mechanism for allowing or preventing flow through the first outflow path 1040. The first outflow path 1040 may also flow through a surgical instrument 1080 before flowing to the vacuum pump 1050. The second outflow path 1060 is an atmospheric outflow path that allows an outflow of fluid $Q_3$ to flow into a receptacle or container 1065. The inflow path 1030, the first outflow path 1040, and the second outflow path 1060 may be made of plastic tubing to interconnect one or more components of the fluid management system 1010.

In use, the inflow pump 1020 pumps one or more fluids through the inflow path 1030 into the uterus U. The inflow pump 1020 may provide a constant flow $Q_1$ of fluid into the uterus U. To control the pressure within the uterus U, the fluid management system 1010 includes the first and second outflow paths 1060 which allows the fluid within the uterus U to flow out of the uterus U. The flow of fluid out of the uterus U is used to control the pressure within the uterus U while the inflow pump 1020 provides the constant flow $Q_1$ into the uterus U.

The fluid management system 1010 includes the first outflow path 1040 which draws fluid from within the uterus U through the vacuum pump 1050 at a flow rate $Q_2$. The vacuum pump 1050 may draw fluid through a surgical instrument 1080. In addition, the fluid management system 1010 may include the switch or valve 1070 to open and close the first outflow path 1040 to control flow of fluid through the first outflow path 1040. The valve 1070 may allow the vacuum pump 1050 to draw a constant vacuum with the flow $Q_2$ being controlled by a position of the valve 1070. The fluid management system 1010 also includes the second outflow path 1060 which allows fluid within the uterus U to flow out at atmospheric pressure and be received in the container 1065 at a flow rate $Q_3$.

Figure 2:
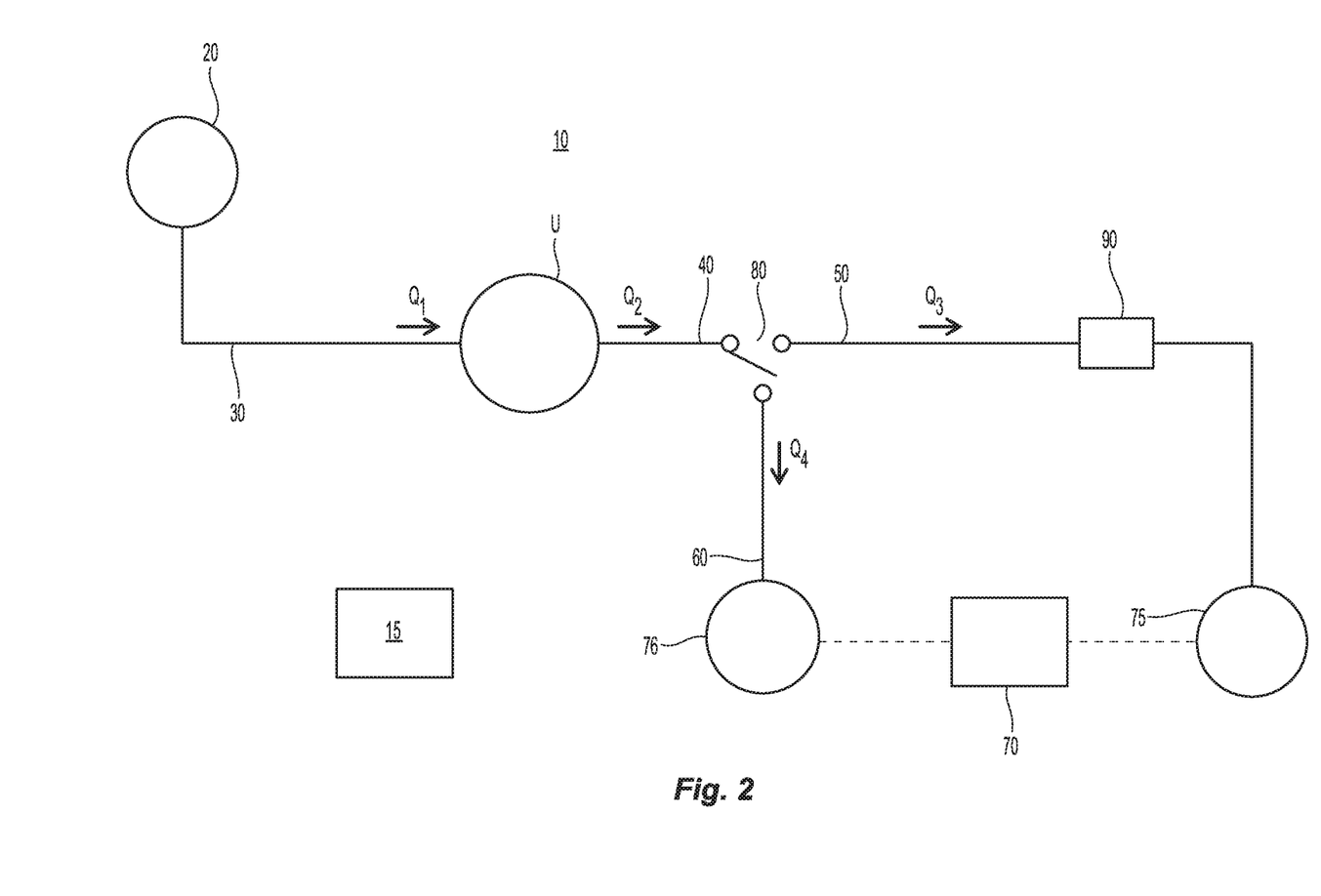
FIG. 2 is a schematic of an exemplary fluid management system for managing intrauterine pressure within a uterus provided in accordance with the present disclosure.

Referring now to FIG. 2, a fluid management system 10 is provided in accordance with the present disclosure and includes an inflow path 30 for providing fluid into a uterus U and a primary outflow path 40. The fluid management system 10 includes an inflow pump 20 that provides a flow of fluid $Q_1$ through the inflow path 30 into the uterus U to increase a pressure within the uterus U. The inflow pump 20 may be a peristaltic pump that provides a substantially constant flow of fluid $Q_1$ into the uterus U. In some embodiments, the inflow pump 20 may have one or more preset settings, e.g., high, medium, or low, for varying the flow of fluid $Q_1$ into the uterus U while being constant at each one of the settings.

The fluid management system 10 uses the primary outflow path 40 to regulate and maintain a desired pressure within the uterus U. The primary outflow path 40 is in fluid communication with the interior of the uterus U and provides a path for fluid to flow out of the uterus U. The flow of fluid out of the uterus U through the primary outflow 40 path is designated as $Q_2$. The flow of fluid $Q_2$ out of the uterus U is the sum of a first outflow $Q_3$ through a first outflow path 50 and a second outflow $Q_4$ through a second outflow path 60. Each of the first and second outflow paths 50, 60 are driven by an outflow pump, e.g., outflow pump 70. The primary outflow path 40 may include a single channel that is divided into the first and second outflow paths 50, 60. Alternatively, the primary outflow path 40 may include two or more channels with one channel in communication with the first outflow path 50 and another channel in communication with the second outflow path 60.

As shown, the first outflow path 50 goes through a first pump head 75 of the outflow pump 70 and the second outflow path 60 goes through a second pump head 76 of the outflow pump. The first outflow path 50 may pass through a surgical instrument 90 before passing through the first pump head 75 of the outflow pump 70. By controlling each of the first and second outflow paths 50, 60 with a pump, e.g., outflow pump 70, greater control of the pressure within the uterus U, intrauterine pressure, may be possible. The outflow pump 70 may be a peristaltic pump as described in greater detail below. In some embodiments, the fluid management system 10 includes a separate outflow pump for each of the first and second outflow paths 50, 60. In addition, by passing each of the first and second outflow paths 50, 60 through a pump, an amount of fluid delivered during a surgical procedure may be reduced and the flow $Q_1$ from the inflow pump 20 may be lower when compared to a fluid management system where one of the outflow paths is vented at atmospheric pressure, e.g., fluid management system 1010 (FIG. 1).

Continuing to refer to FIG. 2, the fluid management system 10 includes a switch or valve 80 between the primary outflow path 40 and the first and second outflow paths 50, 60. The valve 80 has a first position in which the primary outflow path 40 is open to the first outflow path 50 and is closed to the second outflow path 60 and a second position in which the primary outflow path 40 is open to the second outflow path 60 and closed to the first outflow path 50. The valve 80 may also have one or more intermediate positions between the first and second position in which the primary outflow path 40 is at least partially open to both the first and the second outflow paths 50, 60. The valve 80 may have discrete positions such that the valve 80 snaps from one position to another position, e.g., the first position to the second position, or the valve 80 may be continually adjustable between the first and second positions. In embodiments, the valve 80 is continually adjustable between the first and second position and has indicia, e.g., tactile or visual, when the valve 80 reaches one or more positions.

The fluid management system 10 may include a controller 15 that is in communication with the outflow pump 70, the valve 80, and/or the inflow pump 20. As described in greater detail below, the controller 15 varies the outflow pump 70, the valve 80, and/or the inflow pump 20 to control an intrauterine pressure of the uterus U. The controller 15 may be disposed on the outflow pump 70, the valve 80, or remote to the outflow pump 70 and the valve 80. The controller 15 may be a single processing unit that controls each component of the fluid management system 10 or the controller 15 may include one or more controllers disposed on the outflow pump 70, the valve 80, and/or the inflow pump 20 and may also include a central controller (not shown) in communication with each of the other controllers. The controller 15 may be in communication with one or more sensors disposed about the fluid management system 10 or in the uterus U to monitor pressures and/or fluid flow at different locations within the fluid management system 10 or the uterus U.

Figure 2A:
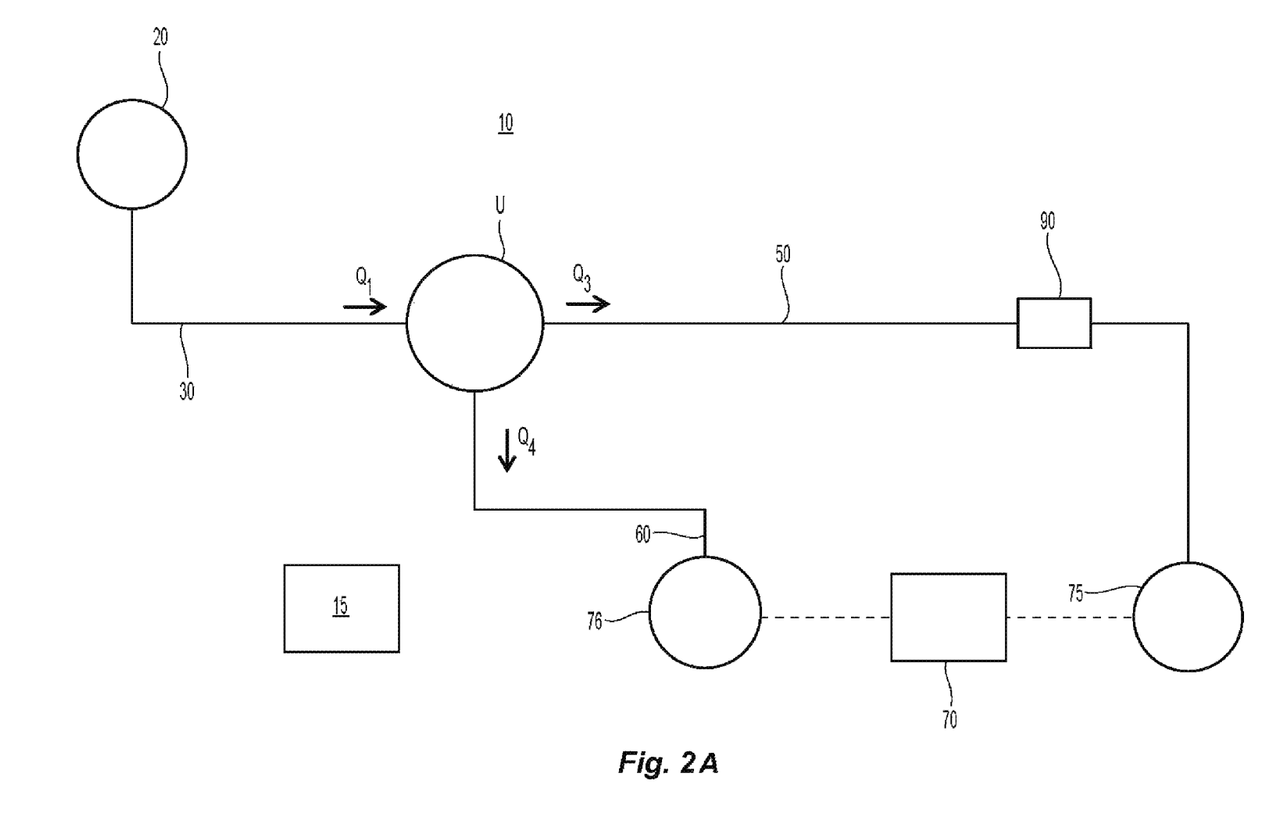
FIG. 2A is a schematic of an alternate embodiment of the exemplary fluid management system for managing intrauterine pressure within a uterus provided in accordance with the present disclosure.

With reference to FIG. 2A, the first and second outflow paths 50, 60 may be directly coupled to the uterus U without the use of the valve 80. In this manner, each of the first and second outflow paths 50, 60 bypass the primary out flow path 40 such that a direct connection is made between each of the first and second outflow paths 50, 60 within the uterus U.

Figure 3:
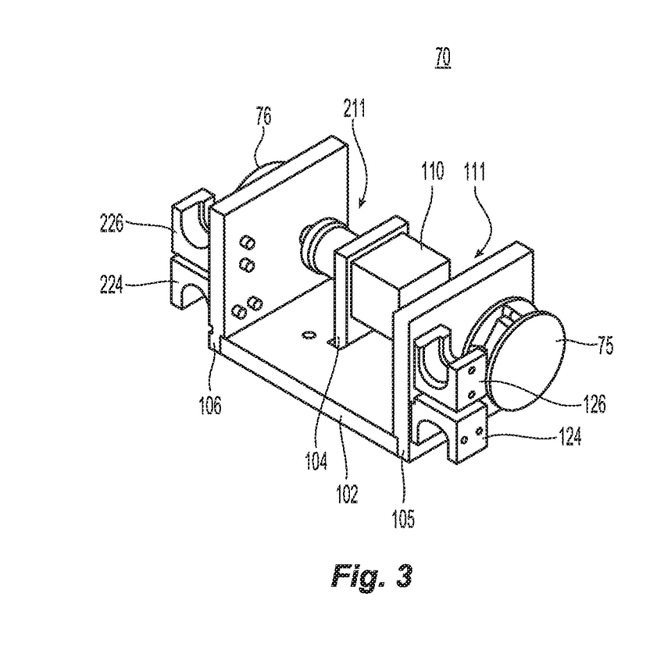
FIG. 3 is a perspective view of a two-headed peristaltic pump of the fluid management system of FIG. 2.
Figure 4:
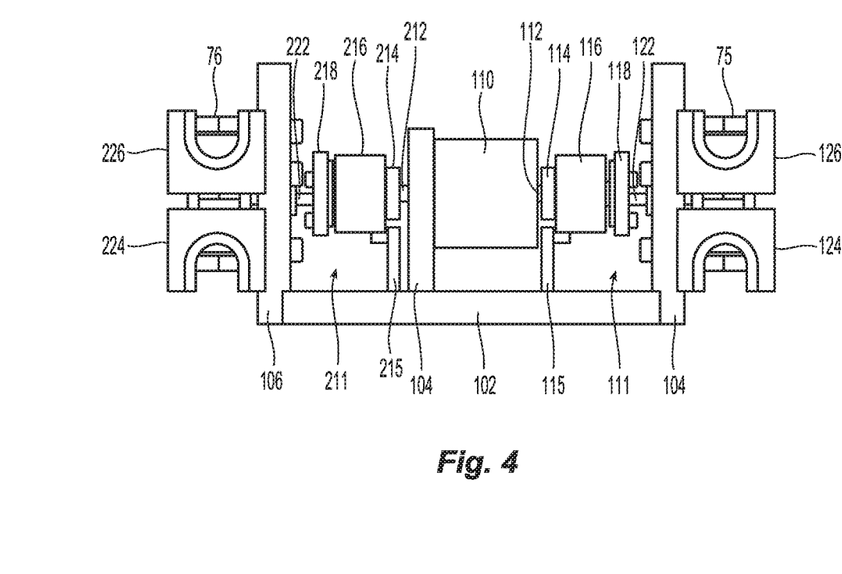
FIG. 4 is a side view of the pump of FIG. 3.

Referring now to FIGS. 3 and 4, the outflow pump 70 includes a motor 110, the first pump head 75 on a first side 111 of the motor 110, and the second pump head 76 on a second side 211 of the motor 110. The outflow pump 70 is configured to independently control rotation of each of the first and second pump heads 75, 76. The motor 110 is secured on a mounting plate 102 by a motor mount 104. The mounting plate 102 includes a first sidewall 105 on the first side 111 of the motor 110 and a second sidewall 106 on the second side 211 of the motor 110. The motor mount 104 is positioned between the first and second sidewalls 105, 106 to secure the motor 110 to the mounting plate 102. The motor mount 104 may be mounted on one side of the motor 110 or may support a central portion of the motor 110. The motor 110 includes a first motor shaft 112 configured to drive the first pump head 75 and a second motor shaft 212 configured to drive the second pump head 76. The first and second motor shafts 112, 212 may be a single shaft that extends entirely through the motor 110.

Elements of the outflow pump 70 are detailed below with elements on the first side 111 of the motor 110 labeled with a leading "1" with similar elements on the second side 211 of the motor 110 labeled with a leading "2", as such only elements on the first side of the motor 110 will be detailed for brevity.

The motor 110 drives the first motor shaft 112 that passes through a first bearing 114 into a transmission or gearbox 116. The first bearing 114 is supported by a bearing mount 115 that extends from the mounting plate 102 between the first and second sidewalls 105, 106. The gearbox 116 converts rotation of the first motor shaft 112 into rotation of a motor side of a clutch 118. The clutch 118 selectively couples rotation of the first motor shaft 112 to rotation of a first drive shaft 122. The first drive shaft 122 is coupled on one end to a drive side of the clutch 118 and on the other end to the first pump head 75 such that when the clutch 118 is engaged, rotation of the first motor shaft 112 causes rotation of the first pump head 75. When the clutch 118 is disengaged, rotation of the first motor shaft 112 is decoupled from rotation of the first pump head 75, i.e., the first pump head 75 is idle. The first drive shaft 112 passes through the first side wall 105 and may include or pass through a bearing (not shown) secured to the first side wall 105.

In use, the first and second pump heads 75, 76 function as peristaltic pumps. Specifically, a tube (not explicitly shown) defining the first outflow path 50 passes through a lower first tube mount 124 that is secured to the first sidewall 105, around the first pump head 75, and through an upper first tube mount 126. Rotation of the first pump head 75 pumps fluid through the tube by compressing a wall of the tube to pump fluid through the first outflow path 50. Similarly, a tube defining the second outflow path 60 passes through a lower second tube mount 224 that is secured to the second sidewall 106, around the second pump head 76, and through an upper second tube mount 226. Rotation of the second pump head 76 pumps fluid through the tube by compressing a wall of the tube to pump fluid through the second outflow path 60. The speed of rotation of the respective pump head 75, 76 and the diameter of the respective pump head 75, 76 determines the flow of fluid $Q_3$, $Q_4$ of each of the first and second outflow paths 50, 60 when the respective pump head 75, 76 rotates.

The controller 15 (FIG. 2) is operably coupled to the first and second clutches 118, 218 to engage/disengage the clutches 118, 218 to control rotation of the first and second pump heads 75, 76. By engaging/disengaging the clutches 118, 218, the motor 110 can rotate both motor shafts 112, 212 simultaneously at the same speed and the controller 15 can selectively engage/disengage the clutches 118, 218 to control rotation of the first and second pump heads 75, 76. For example, the controller 15 may engage the first clutch 118 such that the first pump head 75 is idle and disengage the second clutch 218 such that the second pump head 76 is rotating. Alternatively, the controller 15 may disengage both clutches 118, 218 such that both pump heads 75, 76 rotate simultaneously.

While the first and second motor shafts 112, 212 rotate at the same speed, the first and second gear boxes 116, 216 and/or the first and second pump heads 75, 76 may be varied such that the first side 118 of the outflow pump 70 may have a fluid flow $Q_3$ that is different from a fluid flow $Q_4$ of the second side 218 of the outflow pump 70. The first and second sides 111, 211 of the outflow pump 70 having different flows allows the controller 15 to control the flow of fluid $Q_2$ out of the uterus U by selectively engaging/disengaging the clutches 118, 218 as detailed below. In embodiments, the first and second gearboxes 116, 216 may have different gear ratios such that when both the clutches 118, 218 are engaged, the first pump head 75 rotates at a different speed from the second pump head 76. Additionally or alternatively, the first and second pump heads 75, 76 may have different diameters such that when the first and second pump heads 75, 76 are rotated the flow $Q_3$ through the first outflow path 50 is different from the flow $Q_4$ of the second outflow path 60.

The controller 15 may also be operably coupled to the valve 80 to move the valve 80 between the first and second positions. The controller 15 may be programmed to operate the valve 80 to close the first outflow path 50 when the first clutch 118 is disengaged such that the first pump head 75 is not being rotated and to operate the valve 80 to close the second outflow path 60 when the second clutch 218 is disengaged such that the second pump head 76 is not being rotated. In addition, the controller 15 may be programmed to operate the valve 80 to one or more intermediate positions such that the flow $Q_2$ is greater than either of the flows $Q_3$, $Q_4$.

Referring briefly back to FIG. 2, in some embodiments the fluid management system 10 includes a surgical instrument 90 disposed in the first outflow path 50. When the surgical instrument 90 is in the first outflow path 50, the first outflow path 50 may be used to cool the surgical instrument 90. When the surgical instrument 90 is in the first outflow path 50, the controller 15 may operate the switch 80 in response to a temperature and/or activation of the surgical instrument 90. Alternatively, with reference to FIG. 2A, if the first and second outflow paths 50, 60 are directly coupled to the uterus U, the controller may engage/disengage the first clutch 118 such that the first pump heat 75 is rotated or stops rotating to control the fluid flow to the surgical instrument 90 in response to a temperature and/or activation of the surgical instrument.

Figure 5:
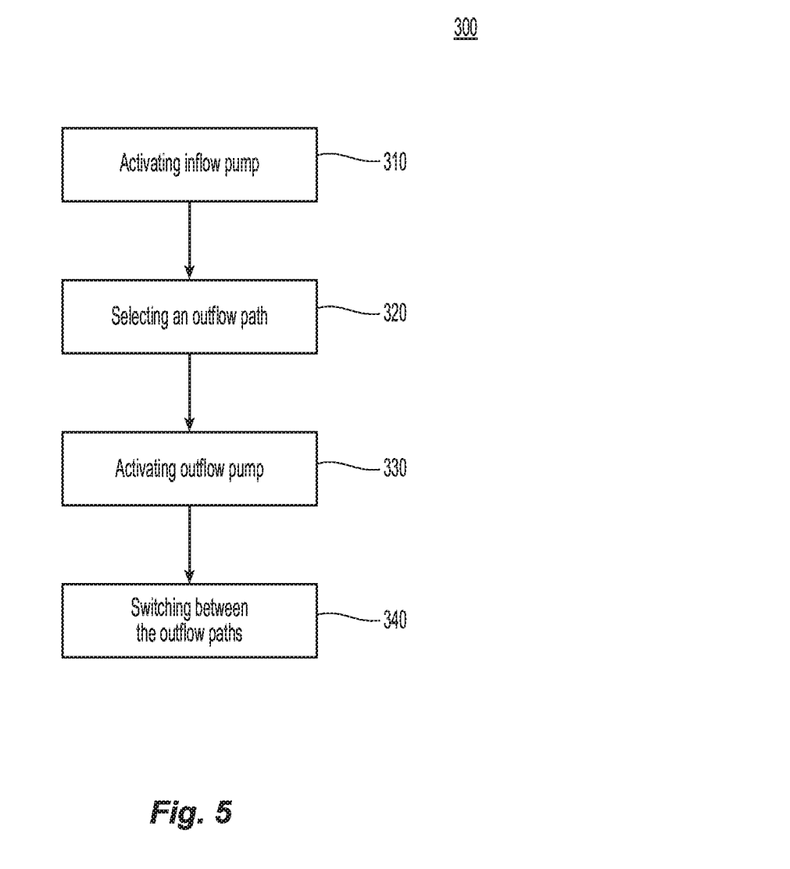
FIG. 5 is a flow chart of a method of controlling the fluid management system of FIG. 2 with the controller.

With reference to FIG. 5, a method 300 of distending a uterus and maintaining a desired intrauterine pressure is disclosed in accordance with the present disclosure with reference to the fluid management system 10 and the outflow pump 70 of FIGS. 2-4. The method 300 may take place in the controller 15 of the fluid management system 10. Initially, the fluid management system 10 is provided with the inflow path 30 in communication with an interior of a uterus U and the primary outflow path 40 in communication with the interior of the uterus U. The inflow and/or primary outflow path 40 may pass through a hysteroscope that is inserted into the vagina to provide access to the cervix and or the inside of the uterus U.

With the inflow path 30 and the primary outflow path 40 in place, the inflow pump 20 is activated to provide a flow of fluid $Q_1$ into the uterus U. The flow of fluid $Q_1$ distends the uterus U and increases the intrauterine pressure (Step 310). The inflow pump 20 is set to a constant flow rate to provide a constant flow of fluid $Q_1$ through the inflow path 30. Using the constant flow of fluid $Q_1$ a volume of fluid into the uterus U can be determined. From the volume of fluid, the intrauterine pressure can be estimated. In some embodiments, a sensor in communication with the interior of the uterus U provides a direct reading of a pressure within the uterus U. The sensor may be disposed on the hysteroscope and may be in communication with the controller 15.

As the uterus U is distended by the flow of fluid $Q_1$, the intrauterine pressure approaches a desired pressure. The desired pressure is a pressure sufficient to distend the uterus U to provide access and/or visualization of an inner surface of the uterus U but below a pressure that may damage the uterus U. As the intrauterine pressure approaches the desired pressure, on outflow path is selected by operating the switch 80 (Step 320). The outflow path may be selected based on a flow of fluid generated by a respective pump head of the pump 70, e.g., first or second pump head 75, 76, or may be selected based on the use or non-use of a surgical instrument 90. For example, before a surgical instrument 90 is inserted through the hysteroscope, the fluid management system 10 may select the second outflow path 60 such that the switch 80 is in the second position. When the outflow path is selected, the switch 80 is operated to be open to the desired one of the first or second outflow paths 50, 60 and the primary outflow path 40 is in communication with the desired outflow path.

With the desired outflow path selected, the outflow pump 70 is activated (Step 330). When the outflow pump 70 is activated, the clutch 118, 218 on the side of the outflow pump 70 that is not open may be disengaged to prevent rotation of the pump head associated with the closed outflow path. Continuing the example above when the second outflow path 60 is open and the first outflow path 50 is closed, the first clutch 118 is disengaged to prevent the first pump head 75 from rotating and the second clutch 218 is engaged such that the second pump head 76 is rotated to generate a flow $Q_4$ of fluid out of the uterus U. In this example, the flow $Q_4$ is equal to the flow $Q_2$.

When the desired pressure is reached, the flow $Q_2$ may be approximately equal to the flow $Q_1$ such that the intrauterine pressure is substantially constant. When the intrauterine pressure is greater than the desired pressure, the flow $Q_2$ through the primary outflow path 40 is increased and when the intrauterine pressure is less than the desired pressure, the flow $Q_2$ is decreased.

To increase or decrease the flow $Q_2$ through the primary outflow path 40, the switch 80 of the fluid management system 10 is operated to switch between outflow paths or to an intermediate position between the secondary outflow paths (Step 340). For example, the flow $Q_3$ may be slightly greater than the flow $Q_1$ such that when the switch 80 is in the second position the flow $Q_2$ through the primary outflow path 40 is greater than the flow $Q_1$ into the uterus U such that the intrauterine pressure is decreased. The switch 80 may be operated to an intermediate position between the first and second positions such that the primary outflow path 40 is partially open to the second outflow path 60 until the flow $Q_2$ is reduced to be equal to the flow $Q_1$. In some embodiments, the flow $Q_3$ may be less than the flow $Q_1$ when the switch 80 is in the first position such that the flow $Q_2$ may need to be increased to prevent the intrauterine pressure from exceeding the desired pressure. In such embodiments, the switch 80 may be moved to an intermediate position such that the primary outflow path 40 is open to both the first and second outflow paths 50, 60 and the first clutch 118 may be engaged such that the first pump head 75 rotates such that a flow $Q_3$ is generated through the first outflow path 50. The switch 80 may be adjusted until the flow $Q_2$ is substantially equal to the flow $Q_1$.

The fluid management system 10 may operate the switch 80 to switch to the first position to switch between outflow paths when a surgical instrument 90 is inserted through the hysteroscope such that fluid flows from the uterus U through the first outflow path 50 which passes through the surgical instrument 90. The flow $Q_3$ through the first outflow path 50 may be used to cool the surgical instrument 90. When the switch 80 is moved to the first position, the flow $Q_3$ may be substantially equal to the flow $Q_1$. In embodiments, the switch 80 may be moved to an intermediate position with a majority of the flow $Q_2$ going through the first outflow path 50 with the remainder of the flow $Q_2$ going through the second outflow path 60 with $Q_2$ being substantially equal to the flow $Q_1$.

Figure 5A:
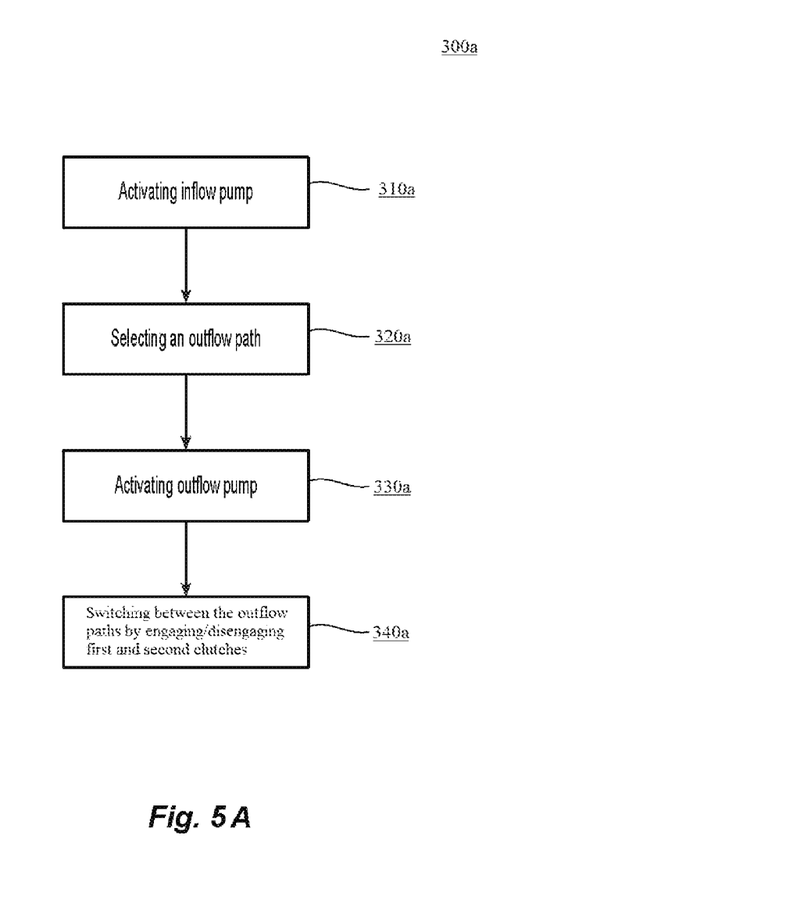
FIG. 5A is a flow chart of a method of controlling the fluid management system of FIG. 2A with the controller.

With reference to FIGS. 2A and 5A, a method 300a of distending a uterus U and maintaining a desired intrauterine pressure is disclosed in accordance with the present disclosure with reference to the fluid management system 10 and the outflow pump 70 of FIGS. 2-4 in a case where the first and second flow paths 50, 60 act directly coupled to the uterus U. The method 300a may take place in the controller 15 of the fluid management system 10. Initially, the fluid management system 10 is provided with the inflow path 30 in communication with an interior of a uterus U and the first and second outflow paths 50, 60 in communication with the interior of the uterus U. The inflow path 30, first outflow path 50, and/or second outflow path 60 may pass through a hysteroscope that is inserted into the vagina to provide access to the cervix and/or the inside of the uterus U.

With the inflow path 30 and each of the first and second outflow paths 50, 60 in place, the inflow pump 20 is activated to provide a flow of fluid $Q_1$ into the uterus U. The flow of fluid $Q_1$ distends the uterus U and increases the intrauterine pressure (Step 310a). The inflow pump 20 is set to a constant flow rate to provide a constant flow of fluid $Q_1$ through the inflow path 30. Using the constant flow of fluid $Q_1$ a volume of fluid into the uterus U may be determined. From the volume of fluid, the intrauterine pressure can be estimated. In some embodiments, a sensor (not shown) in communication with the interior of the uterus U provides a direct reading of the pressure within the uterus U. The sensor may be disposed on the hysteroscope (not shown) and may be in communication with the controller 15.

As the uterus U is distended by the flow of fluid $Q_1$, the intrauterine pressure approaches a desired pressure. The desired pressure is a pressure sufficient to distend the uterus U to provide access and/or visualization of an inner surface of the uterus U but below a pressure than may damage the uterus U. As the intrauterine pressure approaches the desired pressure, an outflow path is selected by the fluid management system 10 (Step 320a). The outflow path may be selected based on a flow of fluid generated by a respective pump head of the pump 70, e.g., first or second pump head 75, 76, or may be selected based on the use or non-use of a surgical instrument 90. For example, before a surgical instrument 90 is inserted through the hysteroscope (not shown), the fluid management system 10 may selectively cause the clutch 218 to be engaged such that the second pump head 76 rotates to cause the flow of fluid $Q_4$ through the second outflow path 60.

With the desired outflow path selected, the outflow pump 70 is activated (Step 330a). In step 340a, when the outflow pump 70 is activated, the clutch 118, 218 on the side of the outflow pump 70 that is not selected may be disengaged to prevent rotation of the pump head associated with the un-selected outflow path. Continuing the example above, when the second outflow path 60 is selected and the first outflow path 50 is not selected, the first clutch 118 is disengaged to prevent the first pump head 75 from rotating and the second clutch 218 is engaged such that the second pump head 76 is rotated to generate a flow $Q_4$ of fluid out of the uterus U.

When the desired pressure is reached, the flow $Q_3$ and/or $Q_4$ may be approximately equal to the flow $Q_1$ such that the intrauterine pressure is substantially constant. When the intrauterine pressure is greater than the desired pressure, the flow $Q_3$ and/or $Q_4$ is increased and when the pressure is less than the desired pressure, the flow $Q_3$ and/or $Q_4$ is decreased.

To increase or decrease the flow $Q_3$ and/or $Q_4$, the fluid management system 10 causes one or both of the clutches 118, 218 to engage/disengage (Step 340a). For example, the combined flow $Q_3$ and $Q_4$ may be slightly greater than the flow $Q_1$ such that the combined flow $Q_3$ and $Q_4$ out of the uterus U is greater than the flow $Q_1$ into the uterus causing the intrauterine pressure to decrease. One of the clutches 118, 218 may be disengaged to stop a respective flow $Q_3$ or $Q_4$ to decrease the total flow out of the uterus U. In some embodiments, the flow $Q_3$ or $Q_4$ may be less than the flow $Q_1$ such that the flow out of the uterus U may need to be increased to prevent the intrauterine pressure from exceeding the desired pressure. In such embodiments, the disengaged clutch 118 or 218 may be engaged such that both clutches 118, 218 are engaged to effectuate both flows $Q_3$ and $Q_4$.

The fluid management system 10 may engage the clutch 118 when a surgical instrument 90 is inserted through the hysteroscope (not shown) such that fluid flows from the uterus U through the first outflow path 50 which passes through the surgical instrument 90. The flow $Q_3$ through the first outflow path 50 may be used to cool the surgical instrument 90. When the clutch 118 is engaged, the flow $Q_3$ may be substantially equal to the flow $Q_1$. In embodiments, both clutches 118, 218 may be engaged to cause flows $Q_3$ and $Q_4$ to flow through respective first and second outflow paths 50, 60, with the combined flows $Q_3$ and $Q_4$ being substantially equal to the flow $Q_1$.

By controlling the flow out of the uterus U by switching between two outflow paths, e.g., first and second outflow paths 50, 60, the methods 300, 300a may allow for greater control of the intrauterine pressure. In addition, when one of the outflow paths, e.g., first outflow path 50, includes a surgical instrument, the method allows for the other outflow path, e.g., second outflow path 60, to be controlled by a pump, e.g., outflow pump 70. Further, by having a single outflow pump 70 with multiple pump heads, the size and the cost of the system may be reduced.

Although generally described has having a single pump 70 with two pump heads 75, 76, the fluid management system 10 may include a single pump with a single pump head. As can be appreciated, the single pump head causes a flow of fluid through both outflow paths 50, 60. Therefore, flow through the outflow paths 50, 60 may be permitted or inhibited by placing or removing a clamp (not shown) or other suitable device on the selected outflow path 50, 60 to close off or otherwise inhibit the flow of fluid therethrough. The clamp may be capable of fully or partially closing the outflow path such that the amount of fluid flow therethrough may be adjusted depending upon the position of the clamp relative to the outflow path.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A pump, comprising:
   a first motor shaft defining a longitudinal axis;
   a second motor shaft, wherein the second motor shaft is longitudinally aligned with the first motor shaft along the longitudinal axis;
   a first pump head operably coupled to the first motor shaft such that the first pump head is rotated in response to rotation of the first motor shaft;
   a second pump head operably coupled to the second motor shaft such that the second pump head is rotated in response to rotation of the second motor shaft; and
   a motor configured to rotate the first and second motor shafts, wherein the motor has a first mode in which the first pump head is rotated and the second pump head is idle and a second mode in which the first pump head is idle and the second pump head is rotated, wherein the first pump head is on a first side of the motor and the second pump head is on a second opposite side of the motor.

2. The pump according to claim 1, wherein the first motor shaft is a first portion of a common motor shaft and the second motor shaft is a second portion of the common motor shaft.

3. The pump according to claim 1, further comprising a first clutch having a motor side operably coupled to the first motor shaft and a drive side operably coupled to the first pump head, the first clutch having an engaged configuration in which the first pump head rotates in response to rotation of the first drive shaft and a disengaged configuration in which the first pump head is decoupled from rotation of the first drive shaft.

4. The pump according to claim 3, wherein the first clutch is in the disengaged configuration when the motor is in the second mode.

5. The pump according to claim 3, further comprising a second clutch having a motor side operably coupled to the second motor shaft and a drive side operably coupled to the second pump head, the second clutch having an engaged configuration in which the second pump head rotates in response to rotation of the second drive shaft and a disengaged configuration in which the second pump head is decoupled from rotation of the second drive shaft.

6. The pump according to claim 3, further comprising a gear box coupled to the first motor shaft and the first clutch, the gear box applying a gear ratio to rotation of the first motor shaft such that rotation of the drive side of the first clutch is different than rotation of the first motor shaft.

7. The pump according to claim 1, wherein the motor has a third mode in which the first pump head and the second pump head are rotated.

8. The pump according to claim 7, wherein in the third mode the first pump head rotates at a different speed than the second pump head.

9. The pump according to claim 1, wherein the first pump head has a first diameter and the second pump head has a second diameter different from the first diameter.

* * * * *